United States Patent [19]
Pierr et al.

[11] Patent Number: 4,668,438
[45] Date of Patent: May 26, 1987

[54] AQUEOUS CONCENTRATES OF SALTS OF α-SULFONATED FATTY ACID ALKYL ESTERS

[75] Inventors: Robert Piorr, Ratingen-Hoesel; Horst Ritterbex, Duesseldorf; Frantisek Jost, Duesseldorf; Hans J. Rommerskirchen, Duesseldorf, all of Fed. Rep. of Germany

[73] Assignee: Henkel Kommanditgesellschaft auf Aktien, Duesseldorf, Fed. Rep. of Germany

[21] Appl. No.: 766,612

[22] Filed: Aug. 16, 1985

[30] Foreign Application Priority Data

Oct. 29, 1984 [DE] Fed. Rep. of Germany ....... 3439520

[51] Int. Cl.$^4$ .................. C07C 143/90; C11D 1/28
[52] U.S. Cl. ........................................... 260/400
[58] Field of Search ........................................ 260/400

[56] References Cited

U.S. PATENT DOCUMENTS 2,878,271  3/1959  Little .................................. 260/400
3,969,375  7/1976  Okumura et al. ..................... 260/400
4,021,460  5/1977  Ogoshi et al. ........................ 260/400
4,404,143  9/1983  Sekiguchi et al. ................... 260/400

FOREIGN PATENT DOCUMENTS 3123681  3/1982  Fed. Rep. of Germany .
3334517  4/1984  Fed. Rep. of Germany .
3305430  8/1984  Fed. Rep. of Germany .

*Primary Examiner*—Charles F. Warren
*Assistant Examiner*—Elizabeth A. Flaherty
*Attorney, Agent, or Firm*—Ernest G. Szoke; Henry E. Millson, Jr.; Real J. Grandmaison

[57] ABSTRACT

Aqueous concentrates of alkali metal salts of α-sulfonated fatty acid alkyl esters (ester sulfonate salts) which are pumpable at temperatures of at least 60° C. are obtained without the addition of viscosity regulators by preparing pastes containing at least about 60% by weight of ester sulfonate salts derived from $C_{16}$ and/or $C_{18}$ fatty acids. More particularly, the concentrates contain less than 10 mole % of ester sulfonate salts with fatty acids containing fewer than 16 carbon atoms. The concentrates are obtained by neutralizing the crude ester sulfonates with concentrated alkali hydroxide solution with intensive cooling at temperatures of at most 90° C.

18 Claims, 2 Drawing Figures

AQUEOUS CONCENTRATES OF SALTS OF α-SULFONATED FATTY ACID ALKYL ESTERS

BACKGROUND OF THE INVENTION

1. Field of the Invention

The present invention relates to pumpable, highly concentrated aqueous pastes of alkali metal salts of α-sulfonated fatty acid alkyl esters and processes for their preparation.

2. Description of Related Art

It is known that α-sulfofatty acid ester salts may be obtained in the form of aqueous pastes by neutralizing α-sulfofatty acid esters, usually with an aqeuous alkali metal hydroxide. The starting materials used are natural fats and/or oils obtained by ester cleavage and subsequent esterification with lower alkanols, more especially methanol, or by transesterifying the natural triglycerides with the lower alkanols. Depending on the origin of the natural starting material, the fatty acid ester mixtures obtained contain a comparatively broad range of fatty acids, normally in the $C_{10}$ to $C_{24}$ range. The sulfonation of these fatty acid ester mixtures, usually with gaseous $SO_3$, leads to more or less heavily discolored, acidic crude sulfonates which have to be bleached and converted into ester sulfonate pastes by neutralization to a pH-value in the range of from about 6 to 7. In this form they are now acquiring increasing practical significance as surfactants and wetting agents for detergents and cleaners based on renewable raw materials of natural origin.

One particular difficulty involved in handling pastes of alkali metal salts of α-sulfonated fatty acid alkyl esters (hereinafter referred to as ester sulfonate salts) is their concentration/viscosity behavior. It is only at comparatively low solids concentrations (for example up to solids contents of approximately 35% by weight) that ester sulfonate salts produced on an industrial scale form, in aqueous mixture, sufficiently fluid solutions or suspensions to guarantee the uninterrupted operation of industrial processes. At higher ester sulfonate salt contents (solids contents of around 40% by weight or higher), the viscosity of the aqueous preparation increases to such an extent that it no longer flows freely. This gives rise to serious limitations, which are discussed below.

Attempts to produce highly concentrated ester sulfonate salt pastes directly by neutralizing the crude sulfonic acid mixture with concentrated alkali metal hydroxide solutions fail because the stirrability and, hence, uniform miscibility of the reaction mixture is lost. At the same time, it becomes impossible to dissipate the heat of neutralization. Local concentration and temperature peaks give rise to undesirable secondary reactions, including in particular the formation of disalts of the α-sulfofatty acids in large quantities through ester cleavage. Another disadvantage is that, understandably, ester sulfonate pastes immobilized by an increase in viscosity can no longer be pumped on an industrial scale. Pipes become blocked and the plant as a whole is brought to a prolonged standstill.

The prior art on ester sulfonate salts pastes of this type is greatly concerned with these particular problems. In particular, it has been proposed to use flow aids and viscosity regulators to improve the flow behavior of aqueous, commercial concentrates of α-sulfofatty acid ester salts. Thus, German Application No. 33 05 430 for example describes the use of $C_8$–$C_{40}$ alcohols which, in addition, may contain one or more hydroxyl groups as substituents and to which up to 20 moles of ethylene oxide and/or propylene oxide per mole of alkanol may be added. These viscosity regulators are added to the ester sulfonate paste in quantities of from 1 to 15% by weight, based on the quantity of surfactant, to adjust the viscosity of the surfactant concentrate to at most 10,000 mPas at 70° C. According to German Application No. 33 34 517, aqueous suspensions containing from 40 to 65% by weight of α-sulfofatty acid ester salt, from 2 to 10% by weight of a lower alcohol sulfate and, optionally, at most 2% by weight of a lower alcohol are said to be sufficiently fluid. These aqueous multicomponent mixtures are obtained by initially preparing aqueous suspensions containing from 30 to 55% by weight of the α-sulfofatty acid ester salt in admixture with from 5 to 15% by weight of a lower alcohol sulfate and from 8 to 40% by weight of a lower alcohol and then concentrating the aqueous suspension to the above-mentioned concentration values. According to German Aplication No. 31 23 681, a highly concentrated aqueous solution of a salt of an α-sulfofatty acid ester may be prepared by neutralizing the crude sulfonic acid in a first stage to pH 2.5–4 with a 15 to 50% by weight aqueous caustic alkali solution in the presence of from 5 to 20% by weight of an alcohol containing up to 4 carbon atoms, adding an aqueous solution diluted to 1–5% by weight of alkali hydroxide to the still acidic partially neutralized product in a following stage and adjusting the pH-value to 6–7.

BREIF DESCRIPTION OF THE DRAWINGS

DESCRIPTION OF THE INVENTION

Figure 1:
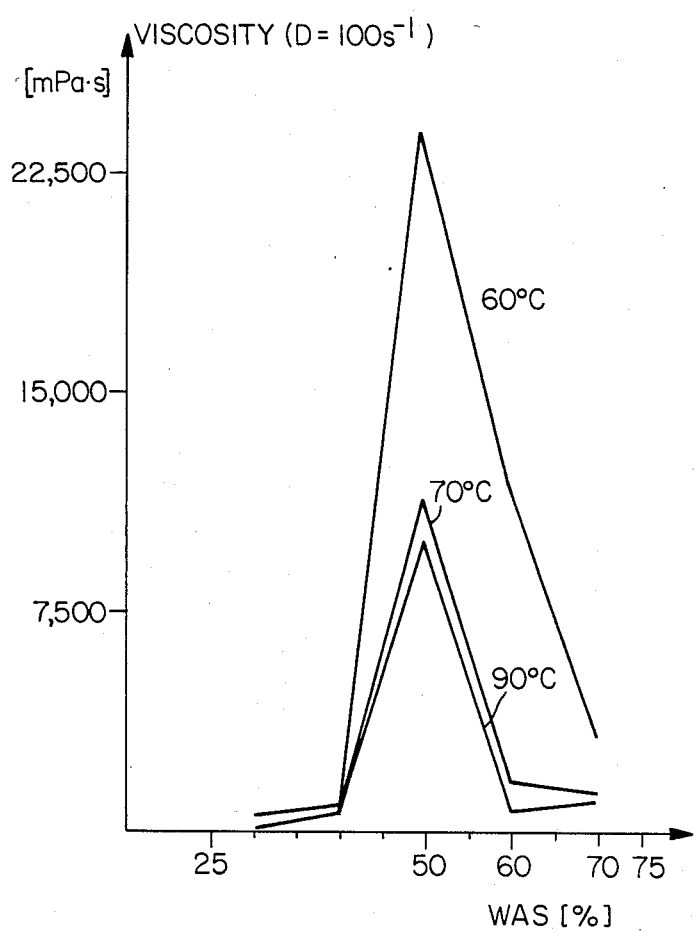
FIG. 1 is a chart showing the dependence of the viscosity of the ester sulfonate salt paste of the present invention on solids content and temperature.

Other than the operating examples, or where otherwise indicated, all numbers expressing quantities of ingredients or reaction conditions used herein are to be understood as modified in all instances by the term "about".

All the known proposals discussed above relate to the usual starting materials of natural origin with a comparatively broad range of chain lengths, for example from $C_{10}$ to $C_{24}$, in the fatty acid mixture. The present invention is based on the surprising observation that, providing certain chain lengths are selected for the fatty acid component of the ester sulfonate salts, anomalies occur in the viscosity behavior of highly concentrated salt pastes in the sense that, after the usual increase in viscosity when the solids content rises beyond about 40% by weight, a solids content is ultimately obtained at which the viscosity values of the highly concentrated, aqueous ester sulfonate salt pastes fall again so drastically that their free flow and, in particular their pumpability at normal processing temperatures are guaranteed.

In a first embodiment, therefore, the present invention relates to aqueous pastes pumpable at temperatures of at least 60° C. and having high contents of alkali metal salts of α-sulfonated fatty acid alkyl esters (ester sulfonate salts), which essentially contain ester sulfonate salts based on $C_{16}$ and/or $C_{18}$ fatty acids, and which have ester sulfonate salt solids contents of at least about 60% by weight and preferably of at least about 65% by weight and, in addition, are substantially free from viscosity regulators or other viscosity-reducing additives.

Accordingly, the teaching of the present invention is based on the surprising discovery that, providing the chain length of the fatty acid component of the ester sulfonate salts is limited to $C_{16}$-$C_{18}$, aqueous suspensions having a particularly high concentration range of, in particular, from 60 to 80% by weight, preferably, from 65 to 80% by weight and more preferably from 70 to 80% by weight, are guaranteed to have free pumpability and miscibility at only moderately elevated temperatures of, for example, from 60° to 70° C. However, if the solids content of the same ester sulfonate salts is reduced to a concentration range of around 40 to 59% by weight, the corresponding aqueous suspensions revert to their familiar concentration-viscosity behavior, i.e. are no longer free-flowing or pumpable. The same applies when the limitation according to the invention with regard to the chain length of the fatty acid component of the ester sulfonate salts is not observed and, for example, the usual starting materials based on fatty acid mixtures having chain lengths of from $C_{12}$ to $C_{18}$ are used. For ester sulfonate salt pastes of the $C_{12}$-$C_{18}$ mixed type, there is no reduction in viscosity in the high solids range of 60 to 80% by weight which enables them to be freely and safely handled without the addition of viscosity regulators or other known measures.

The presence in small quantities of fatty acids or fatty acid esters having chain lengths outside the desired range, of the type which can accumulate in the working up of natural fatty acid mixtures on an industrial scale, need not necessarily by troublesome. However, ester sulfonate salt pastes suitable for use in accordance with the invention contain those fatty acids outside the $C_{16}$-$C_{18}$ range and, in particular, fatty acid esters of shorter chain length in quantities of at most up to 10 mole % and preferably in quantities of distinctly less than 10 mole %. The mixing ratios of $C_{16}$ to $C_{18}$ fatty acids are preferably from 3:2 to 0:1 and, more preferably, from 3:2 to 1:2. A particularly important starting material for obtaining the highly concentrated and yet pumpable ester sulfonate salt pastes according to the invention are fatty acid esters, particularly fatty acid methyl esters, in which the mixing ratio of $C_{16}$ to $C_{18}$ is of the order of 1:1.

Industrial starting materials with the requisite mixing ratios for the number of carbon atoms in the fatty acid component accumulate in certain processes for working up natural fats and/or oils. Thus, the production of oleic acid by splitting tallow using the so-called preferential wetting process or the working-up of palm oil leads to a product which contains the $C_{16}$ and $C_{18}$ fatty acids in a ratio of approximately 1:1. Accordingly, this product is a particularly suitable starting material for the purposes of the present invention. The production of so-called palm stearin from palm oil leads to fatty acid or fatty acid ester mixtures having a $C_{16}$ to $C_{18}$ ratio of about 60:40. The fatty acid cuts which accumulate in the working up of tallow frequently have a $C_{16}$:$C_{18}$ ratio of 1:2 with only slight impurities in the form of other fatty acids. Hardened soya oil has a $C_{16}$:$C_{18}$ mixing ratio of about 8:92. These starting materials are also suitable for the purposes of the present invention. By contrast, other standard fats and oils containing fatty acid mixtures, for example having chain lengths of from $C_{12}$ to $C_{18}$, and at the same time only limited quantities of fatty acids within the $C_{16}$-$C_{18}$ range do not produce lower viscosities when converted into ester sulfonate salt pastes having a solids content of 60% by weight and higher.

The pH-value of the highly concentrated aqueous ester sulfonate salt pastes of the invention is preferably in the range from 6 to 7. The viscosity of the pastes as determined by rotational viscosimeter generally does not exceed about 10,000 mPas at 70° C. The content of disalts is determined primarily by the mixing ratios selected for the ester sulfonation stage. The ester sulfonation stage is normally carried out with an approximately 20% excess of $SO_3$ which, after neutralization with no other measures, leads to a disalt content of from 20 to 25% by weight, based on washing-active substance (WAS). Disalt contents of this order do not affect the desired viscosity behavior of the highly concentrated ester sulfonate salt pastes. If desired, however, the disalt content can be limited in known manner and, more particularly, in accordance with U.S. Application Serial No. 753,304, entitled "CONTROL OF DISALT IN α-SULFOFATTY ACID ESTER SURFACTANTS", filed July 10, 1985.

Figure 2:
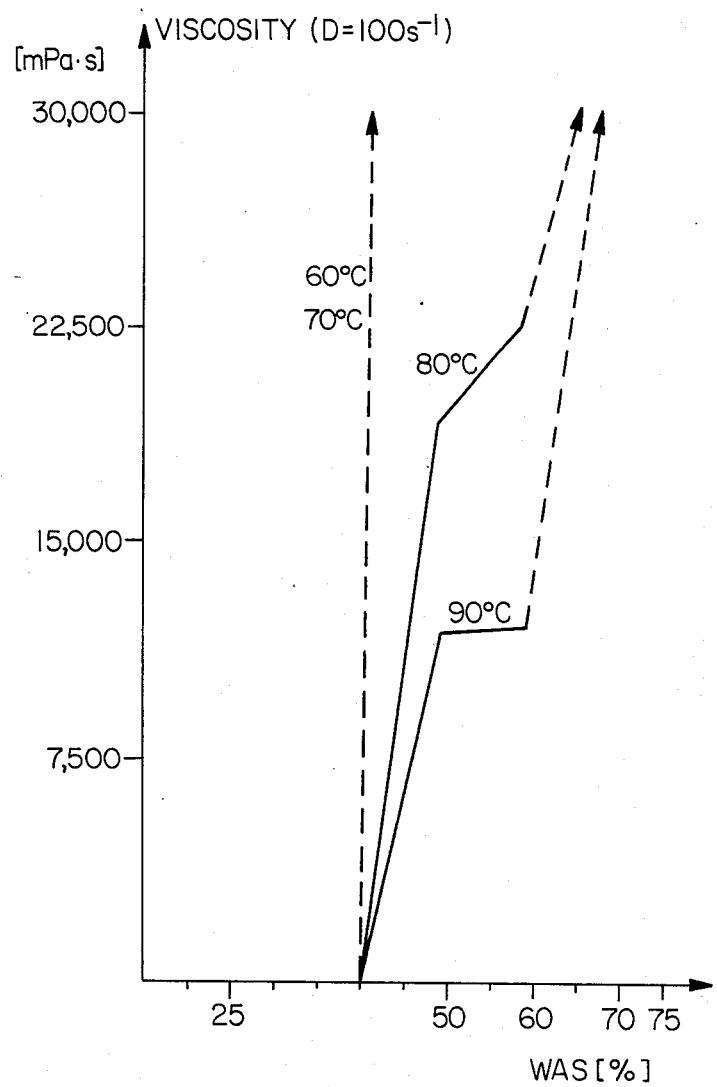
FIG. 2 is a chart showing the relationship between viscosity of an ester sulfonate salt paste derived from a commercial palm kernel oil and the solids content and temperature.

FIG. 1 of the drawings shows the dependence of the viscosity behavior of an ester sulfonate salt paste of the invention on the solids content (% WAS) with the temperature dependence in the range of from 60° to 90° C. also being clearly apparent. The ester sulfonate salt of FIG. 1 contains α-sulfonated fatty acid methyl ester with a mixing ratio of $C_{16}$ to $C_{18}$ of about 1:1, of the type which accumulates as co-product in the splitting of tallow by the preferential wetting process. FIG. 1 shows that, beginning at a solids content of 40% WAS, there is a steep increase in viscosity—shear viscosity ($D=100$ $s^{-1}$)—which reaches its maximum at about 50% WAS. When the solids content of the paste is further increased, viscosity falls and, between 60 and 75%, reaches WAS values which subsantantially correspond to the viscosity behavior of a 30 to 40% ester sulfonate salt paste. By contrast, FIG. 2 of the accompanying drawings illustrates the dependence of the viscosity behavior of an ester sulfonate salt paste derived from a commercial palm kernel oil containing a $C_{12}$-$C_{18}$ fatty acid cut, wherein the $C_{12}$-$C_{14}$ fatty acid component makes up at least about 70%. Starting at about 40% WAS, there is again a steep increase in viscosity, although no reduction in viscosity occurs when the solids content limits of 50% and 60% WAS are exceeded.

The discovery on which the present invention is based not only enables selected ester sulfonate salt pastes of high solid ooncentrations to be safely handled, but the teaching of the invention is particularly important for the production of highly concentrated ester sulfonate salt pastes. The difficulties arising out of the neutralization reaction and the undesirable thickening occurring as a result (producing inconsistencies in the reaction and also secondary reactions), which were hitherto regarded as unavoidable, can be safely eliminated in accordance with the invention. In the embodiment of the invention described hereinafter, it is possible to directly obtain ester sulfonate pastes of high solids content by neutralizing the crude sulfonic acids with highly concentrated solutions of an alkali metal hydroxide, particularly sodium hydroxide. In this further embodiment, therefore, the present invention relates to a process for producing the highly concentrated ester sulfonate salt pastes wherein, after an optional acidic bleaching in known manner, more especially with $H_2O_2$, the crude ester sulfonates are neutralized with intensive cooling at temperatures not in excess of 90° C. to a pH-value of from about 6 to 7 using concentrated aqueous alkali hydroxide solution to form ester sulfonate salt pastes having a solids content of at least about 60% by weight, which if desired are subjected to another bleaching treatment, preferably with NaOCl. To this end, the crude ester sulfonates and the concentrated aqueous alkali metal hydroxide solution are preferably fed into an intensively stirred and cooled ester sulfonate paste of high solids content, preferably at least about 60% by weight WAS, so that neutralization takes place with salt formation within the desired, comparatively low viscosity aqueous ester sulfonate salt paste.

In the practical application of this neutralization process, it is important that the reaction mixture should be sufficiently cooled to dissipate the heat of neutralization so that the temperature does not exceed or significantly exceed an upper limit of the order of 90° C. Neutralization temperatures of from 60° to 90° C. are particularly suitable. It is also preferred to limit the residence time (in continuous processes, the average residence time) of the reaction medium at temperatures in the above range. The residence time or average residence time is preferably not more than 30 minutes and, preferably, less than about 20 minutes. By maintaining the above temperatures and residence times, coupled with the intensive mixing of the suspension which is made possible by its low viscosity, the alkali hydroxide and crude sulfonic acid can by uniformly mixed into the ester sulfonate paste, thus precluding any local differences in concentration and/or temperature. In addition, problems arising out of immobilization of the reaction mixture through excessive viscosity are ruled out by the fact that the WAS solids content of the reaction medium is adjusted from the outset to such high concentrations that the low viscosity required prevails.

Using the process of the invention, optionally prebleached crude sulfonates can be directly converted into free-flowing, fully neutralized ester sulfonate salt pastes having a pH-value of from 6 to 7 with aqueous alkali hydroxide solutions having a concentration in the range of, for example, from 15 to 70% by weight and, preferably, from 30 to 55% by weight. The process of the invention lends itself to modification in various ways. In one preferred embodiment, neutralization is carried out continuously in a reaction loop through which a $C_{16}$-$C_{18}$ ester sulfonate salt paste in accordance with the invention, with solids contents of at least 60% by weight, is circulated and cooled. On the one hand, α-sulfonated fatty acid esters within the above-mentioned chain-length range and aqueous neutralizing agent are introduced into this reaction loop while, on the other hand, a corresponding proportion of ester sulfonate paste is removed therefrom. The temperature in the neutralization loop is kept, for example, in the range of from 80° to 90° C. If the crude sulfonic acid is subjected in known manner to acidic bleaching with $H_2O_2$ before neutralization, it may be advisable to place the neutralization circuit under pressure, for example under a pressure of up to 10 bars. If desired, the proportions of ester sulfonate paste removed from the neutralization circuit may be subjected to another bleaching treatment with NaOCl in the neutral range.

However, instead of reacting the alkali hydroxide and crude sulfonate in the neutralization cycle described above, neutralization can also be carried out in intensively stirred and cooled reactors already containing sufficient quantities of ester sulfonate paste. In this case, the process can be carried out in batches or continuously.

Viscosity problems arising at the beginning of a continuous process can readily be overcome as follows:

At the beginning of the neutralization reaction, a viscosity regulator is added to the reaction mixture and, at the same time, sufficiently dilute reaction solutions are used, so that undesirable immobilization is safely prevented. Low-solids and/or viscosity-regulated ester sulfonate salt pastes such as these are concentrated in their ester sulfonate salt content while more viscosity regulator is continuously introduced. The viscosity of the pastes is best always kept at values of at most 10,000 mPas at 70° C. After the viscosity of the paste has reached its maximum at a solids content of about 50% by weight WAS, it falls as the solids content continuous to increase. The addition of viscosity regulator can now be reduced until, in the desired concentration range of the ester sulfonate salt paste, there is no longer any need for viscosity regulation. At the same time, provision is made by the introduction of highly concentrated reactants (above all highly concentrated aqueous alkali hydroxide solution), to ensure that the solids content of the reaction medium remains in the desired range.

The invention will be further illustrated, but not limited, by the following example.

EXAMPLE

In a continuous sulfonation reactor, 42.5 kg/h (=150 moles/h) of hardened tallow fatty acid methyl ester ($C_{16}$:$C_{18}$ 1:1), from which the oleic acid had been removed before hardening by separation using the preferential wetting process, were reacted with 14.4 kg/h (=180 moles/h) of $SO_3$ diluted to 5% by volume with dry air to form α-sulfonated tallow fatty acid methyl ester.

This sulfonation mixture was delivered at 80° C. to a continuous neutralization stage initially filled with water. At the same time, 50% sodium hydroxide solution was introduced to give a pH-value of from 5 to 7. The temperature was kept at 80° to 90° C. by cooling. The neutralized product was recirculated and thus concentrated. Beyond an active substance (AS) content of about 25% by weight in the neutralized product, from 5 to 8.5 kg/h of $C_{28}$ Guerbet alcohol (10 to 15%, based on AS) were introduced to reduce viscosity until the solids concentration reached 55 to 60% AS. Thereafter, the addition of the Guerbet alcohol was reduced in stages to 0% and the neutralized product adjusted to a solids concentration of approximately 70% AS. The highly concentrated paste was pumped without difficulty at temperatures in the range of from 60° to 90° C.

What is claimed is:

1. An aqueous paste which can be readily pumped at a temperature of about 60° C. or higher consisting essentially of water and an alkali metal salt of an α-sulfonated fatty acid alkyl ester in which the fatty acid moiety therein is a $C_{16}$ fatty acid or a $C_{18}$ fatty acid, or a mixture of such salts, wherein said paste has an ester sulfonate salt solids content of at least about 60% by weight, based on the weight of the paste, and said paste has a viscosity not in excess of 10,000 mPas at a temperature of from about 60° to about 70° C.

2. A process for preparing the aqueous paste of claim 1 comprising neutralizing a crude bleached or unbleached α-sulfonated fatty acid alkyl ester in which the fatty acid moiety is a $C_{16}$ fatty acid, a $C_{18}$ fatty acid, or a mixture of such esters with a concentrated aqueous alkali metal hydroxide solution to form an ester sulfonate salt paste having a solids content of at least about 60% by weight, while intensively cooling the neutralizing mixture at a level not exceeding about 90° C.

3. A process in accordance with claim 2 wherein the paste has a solids content of from about 60 to about 80% by weight.

4. A process in accordance with claim 2 wherein the crude α-sulfonated fatty acid alkyl ester sulfonate and the concentrated aqueous alkali metal hydroxide solution are introduced into an intensively stirred and cooled ester sulfonate salt paste having a solids content of at least 60% by weight, and wherein the average residence time of this reaction mixture under the temperature conditions of the neutralization reaction is no more than about 20 minutes.

5. A process in accordance with claim 2 wherein the concentrated aqueous alkali metal hydroxide solution is a sodium hydroxide solution.

6. A process in accordance with claim 2 wherein the concentration of the aqueous alkali metal hydroxide solution is in the range of from about 15 to about 50% by weight.

7. A process in accordance with claim 2 wherein the neutralizing reaction is carried out continuously in a reaction loop through which the ester sulfonate salt paste is circulated and cooled, by continuously introducing alkali metal hydroxide solution and crude ester into the loop while continuously removing from the loop a corresponding proportion of ester sulfonate salt paste.

8. A process in accordance with claim 7 wherein at the beginning of the neutralizing reaction a viscosity reducing agent and water are also added to maintain the viscosity of the ester sulfonate salt paste at a level no greater than about 10,000 mPas at 70° C. until the concentration of solids in the ester sulfonate salt paste reaches about 60% by weight, and then discontinuing the addition of the viscosity reducing agent and the water.

9. A process for preparing the aqueous paste of claim 1 comprising neutralizing a crude bleached or unbleached alpha-sulfonated fatty acid alkyl ester with a concentrated aqueous alkali metal hydroxide solution to form an ester sulfonate paste having a solids content of at least about 60% by weight, while intensively cooling the neutralizing mixture at a level not exceeding about 90° C., carrying out the neutralizing reaction and the cooling continuously in a reaction loop through which the ester sulfonate salt paste is circulated and cooled, by continuously introducing said alkali metal hydroxide solution and said crude ester into said loop while continuously removing from said loop a corresponding proportion of ester sulfonate salt paste, wherein at the beginning of the neutralizing reaction a viscosity reducing agent and water are also added to maintain the viscosity of the ester sulfonate salt paste at a level no greater than about 10,000 mPas at 70° C. until the concentration of solids in the ester sulfonate salt paste reaches about 60% by weight, and then discontinuing the addition of the viscosity reducing agent and the water.

10. A process in accordance with claim 9 wherein said viscosity reducing agent is a $C_{28}$ Guerbet alcohol.

11. An aqueous paste which can be readily pumped at a temperature of about 60° C. or higher consisting essentially of water and an alkali metal salt of an alpha-sulfonated fatty acid alkyl ester in which the fatty acid moiety therein is a $C_{16}$-fatty acid or a $C_{18}$-fatty acid, or a mixture of such salts, wherein said salt is present in said paste in at least about 60% by weight, based on the weight of said paste, said paste having been prepared by neutralizing a crude bleached or unbleached alpha-sulfonated fatty acid alkyl ester with a concentrated aqueous alkali metal hydroxide solution to form an ester sulfonate paste having a solids content of at least about 60% by weight, while intensively cooling the neutralizing mixture at a level not exceeding about 90° C., carrying out the neutralizing reaction and the cooling continuously in a reaction loop through which the ester sulfonate salt paste is circulated and cooled, by continuously introducing said alkali metal hydroxide solution and said crude ester into said loop while continuously removing from said loop a corresponding proportion of ester sulfonate salt paste, wherein at the beginning of the neutralizing reaction a viscosity reducing agent and water are also added to maintain the viscosity of the ester sulfonate salt paste at a level no greater than about 10,000 mPas at 70° C. until the concentration of solids in the ester sulfonate salt paste reaches about 60% by weight, and then discontinuing the addition of the viscosity reducing agent and the water.

12. An aqueous paste in accordance with claim 11 wherein the ratio of $C_{16}$ to $C_{18}$ fatty acid moieties in the ester salt is from about 3:2 to 0:1.

13. An aqueous paste in accordance with claim 12 wherein said ratio is from about 3:2 to about 1:2.

14. An aqueous paste in accordance with claim 11 wherein the alkyl group in the alkali metal salt is the methyl group.

15. An aqueous paste in accordance with claim 11 wherein said salt is present in an amount of from about 60 to about 80% by weight.

16. An aqueous paste in accordance with claim 11 wherein said salt is present in an amount of from about 65 to about 80% by weight.

17. An aqueous paste in accordance with claim 11 wherein the pH is from about 6 to about 7.

18. An aqueous paste in accordance with claim 11 wherein no more than about 25% of the active ingredients therein are disalts.

* * * * *